US008614366B2

(12) United States Patent
Wilson

(10) Patent No.: US 8,614,366 B2
(45) Date of Patent: *Dec. 24, 2013

(54) METHODS FOR GENETIC PLANT TRANSFORMATION USING WATER-SOLUBLE FULLERENE DERIVATIVES

(76) Inventor: Stephen R. Wilson, Danville, VA (US)

( * ) Notice: Subject to any disclaimer, the term of this patent is extended or adjusted under 35 U.S.C. 154(b) by 364 days.

This patent is subject to a terminal disclaimer.

(21) Appl. No.: 12/876,671

(22) Filed: Sep. 7, 2010

(65) Prior Publication Data

US 2011/0059529 A1    Mar. 10, 2011

Related U.S. Application Data

(60) Provisional application No. 61/240,229, filed on Sep. 6, 2009.

(51) Int. Cl.
*C07K 14/415* (2006.01)
*B82Y 30/00* (2011.01)

(52) U.S. Cl.
USPC ........... 800/278; 800/285; 800/292; 800/293; 800/294; 423/445 B; 430/916

(58) Field of Classification Search
None
See application file for complete search history.

(56) References Cited

U.S. PATENT DOCUMENTS

| | | | |
|---|---|---|---|
| 5,648,523 | A | 7/1997 | Chiang |
| 6,399,785 | B1 | 6/2002 | Murphy et al. |
| 6,765,098 | B1 | 7/2004 | Nakamura et al. |
| 7,163,956 | B2 | 1/2007 | Wilson et al. |
| 2010/0248373 | A1* | 9/2010 | Baba et al. ............... 435/468 |

FOREIGN PATENT DOCUMENTS

| | | | |
|---|---|---|---|
| WO | WO 2006078640 | A2 * | 7/2006 |
| WO | 2008156021 | | 12/2008 |

OTHER PUBLICATIONS

Khodakovskaya et al., Carbon Nanotubes Are Able to Penetrate Plant Seed Coat and Dramatically Affect Seed Germination and Plant Growth, ACS NANO, vol. 3, No. 10, 2009.
Cassell et al., Assembly of DNA/Fullerene Hybrid Materials, Angrew. Chem. Int. Ed. 1998, 37, No. 11.
Herrero et al., Synthesis and Characterization of a Carbon Nanotube-Dendron Series for Efficient siRNA Delivery, JACS Articles, J. Am. Chem. Soc. 2009, 131.
Cai et al., Highly efficient molecular delivery into mammalian cells using carbon nanotube spearing, Nature Methods, vol. 2 No. 6, Jun. 2005.
Liu et al., Preparation of fluorescence starch-nanoparticle and its application as plant transgenic vehicle, J. Cent. South Univ. Technol. (2008) 15: 768-773.
Klumpp et al., Multifunctionalised cationic fullerene adducts for gene transfer: design, synthesis and DNA complexation, ChemComm, The Royal Society of Chemistry 2007.
Isobe et al., Gene Delivery by Aminofullerenes: Structural Requirements for Efficient Transfection, InterScience, 2006 Wiley-VCH Verlang GmbH & Co. KGaA, Weinheim.
Dan, Biological functions of antioxidants in plant transformation, The Society for in Vitro Biology 2008, Apr. 7, 2011.
Boutorine et at., Fullerene-Oligonucleotide Conjugates: Photo-induced Sequence-Specific DNA Cleavage, Angew. Chem. Int. Ed. Engl. 1994, 33, No. 23/24.
Gao et al., Carbon Nanotube Delivery of the GFP Gene into Mammalian Cells, InerScience, ChemBioChem 2006, 7, 239-242.
Nakamura et al., Functionalized Fullerene as an Artificial Vector for Transfection, Angew. Chem. Int. Ed. 2000, 39, No. 23.
Sitharaman et al., Water-Soluble Fullerene (C60) Derivatives as Nonviral Gene-Delivery Vectors, Molecular Pharmaceutics, vol. 5, No. 4, 2008.
Torney et al., Mesoporous silica nanoparticles deliver DNA and chemicals into plants, nature nanotechnology, vol. 2, May 2007.
Nair et al., Nanoparticle material delivery to plants, Plant Science, Elsevier, 2010.
Wikipedia, Allotropes of Carbon, http://en.wikipedia.org/wiki/Allotropes_of_Carbon, Apr. 4, 2013, p. 1-10.

* cited by examiner

*Primary Examiner* — David T Fox
*Assistant Examiner* — Jared Shapiro
(74) *Attorney, Agent, or Firm* — James G. Passé; Passé Intellectual Property, LLC

(57) ABSTRACT

In various embodiments, methods described herein comprise the use of water-soluble cationic fullerene derivatives for improving plant genetic transformation. Cationic Fullerene derivatives of the invention possess DNA binding and compaction activity and provide a new method to deliver DNA into plant cells for plant transformation. Water-soluble fullerene derivatives of the invention with anionic or non-polar substituents possess antioxidant (free radical scavenging) activity, provide improved yields and efficiency of plant transformation methods such as biolistic, *Agrobacterium tumefaciens*, or electroporation methods by limiting cellular damage and resulting cell death leading to higher yields of viable transformed cells in the process.

12 Claims, 9 Drawing Sheets

1. n = 12-16

2

3 (n = 3)
4 (n = 4)
5 (n = 5)

6

A

B

METHODS FOR GENETIC PLANT TRANSFORMATION USING WATER-SOLUBLE FULLERENE DERIVATIVES

This application claims priority of U.S. provisional application No. 61/240,229, filed on Sep. 6, 2009 and is incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The invention relates to methods for inserting new genes into plants using water-soluble fullerene derivatives and to protecting plants from damage during the transformation process.

2. Description of Related Art

Genetic engineering of plant cells differs significantly from that of animal cells because of the unique characteristics of the plant cell which has a protective barrier called the cell wall. The methods used to transform animal cells and protoplasts are simply ineffective. Because of the cell wall barrier, which is made of polysaccharides and other polymers, special plant genetic transformation methods have been developed that use a physical, chemical, or biological agents to deliver DNA into cells. One such method is called the gene gun or biolistics. Using this technique, DNA is first bound to tungsten or gold micro-projectiles (micron sized particles) which are then loaded onto a carrier. The DNA coated particles are placed into a "gene gun" which contains a high pressure helium rupture disk, and a stopping screen. When the helium pressure is raised, the disk breaks and the DNA/particles are literally blasted into plant cells. Details of the method are well known in the art.

A second important approach uses the bacteria *Agrobacterium tumefaciens* for gene transfer. This method comprises inserting the gene of interest into *Agrobacterium tumefaciens*. The next step involves infecting the plant cells with the bacteria which infects the plant and, in favorable cases, the gene of interest is inserted into the plant genome leading to a transformed cell. The next step involves growing the transformed cells in culture to produce plantlets, and then planting and growing the final transformed plant.

Several other methods for plant transformation are less commonly used, such as electroporation. The first step involves suspending the DNA and plant cells or protoplasts in buffer and placing the mixture into a cuvette containing electrodes. Electrical impulses are applied to the suspension to increase membrane and cell wall permeability to DNA, resulting in some DNA moving into the cells, giving transformed cells.

Other methods are (1) microinjection (direct injection of DNA into the cell nucleus using an ultrafine needle), and (2) treatment of plant cells with a permeability agent such as the chemical polyethylene glycol which renders the cell membrane permeable, allowing uptake of DNA from the surrounding solution.

All plant transformation methods are damaging to plant cells and do not work in all cases. In addition, the yield or efficiency, or the DNA insertion process is often low especially because of the damage done to the plant cell or protoplast during the transformation.

Nanomaterial and nanoparticles have wide uses in biology. Because a variety of nanoparticle core materials are available with tunable surface properties, nanoparticles are an excellent platform for a broad range of biological and biomedical applications.

Fullerene nanomaterials are a special class and fullerenes are cage-like, hollow molecules composed of hexagonal and pentagonal groups of carbon atoms that constitute the third form of carbon after diamond and graphite. Fullerene derivatives which have a surface of the fullerene cage can be functionalized by a wide range of groups.

Uses of water-soluble fullerene derivatives have resulted in a wide range of applications. In particular, fullerene derivatives of C60 or C70 have been found to have excellent properties for use in medicine.

Fullerene compounds have been used as delivery vehicles for inserting DNA into animal cells. Certain fullerene derivatives containing positive charges (cationic fullerenes) and can interact with DNA, some fullerene derivatives have been shown to be effective in transfection—the introduction of new DNA into animal cells. An example is the complexation of GFP plasmid with polyamino-fullerene derivatives and demonstration of transfection into COS-1 cells. The application of several other fullerene compounds for transfection in 3T3 cells is also known. Plant cell molecular biology is different because of the plant cell wall barrier and what is effective for animal cells is usually not effective for plants and plant cells. Accordingly, the value of the present invention could not have been known absent the disclosure that the results of the invention were positive and robust.

Only a few reports have appeared concerning the application of nanomaterials on plants and even fewer on the use of fullerene nanomaterials to plants. A comprehensive recent review of plant biotechnology had a single specific mention of nanomaterials application to plants. Reports describe the use of mesoporous silica nanoparticles for gene delivery in plant transformation. A more recent approach used starch nanoparticles coated with poly-L-lysine, as a water-in-oil microemulsion, for plant transformation. One recent paper describes the growth of tomato seeds in media containing relatively high concentrations of multi-wall carbon nanotubes (10-40 microG/mL). Seed germination times were shortened and growth was created that of un-treated seeds.

Antioxidants have been shown to enhance the efficacy of plant transformation and the topic has been recently reviewed. For example, it has been investigated that the effects of antioxidants on transformation efficacy during peanut *Agrobacterium*-mediated transformation. They found that glutathione, tocopherol, and selenite not only eliminated the formation of H2O2 (produced in wound tissue during preparation of leaf explants), but also enhanced the activities of antioxidant enzymes such as superoxide dismutase (SOD) and catalase (CAT). Transformation frequencies could be increased from 3.9% (no antioxidant) to 14.6% (glutathione), 10.3% (tocopherol), and 12.4% (selenite) respectively. Fullerene derivatives as free radical scavengers have been extensively explored, however, their exceptional effect in protecting plant cells, especially during DNA transformation, was more of an effect than would be expected since such effect is not taught even in animal cells. In fact, since plant cells are so different than animal cells, one skilled in the art could not even predict that the compounds of the present invention would have any positive effect in plant cells let alone the surprising and unexpected protection and repair of plant cells during the process of DNA transformation.

BRIEF SUMMARY OF THE INVENTION

In various embodiments, methods described herein provide compounds, reagents, and methods to insert new genetic material into plant cells. The invention encompasses water-soluble fullerene derivatives complexed with selected DNA compositions for genetic modification of plants. The free radical scavenging activity provides a novel method to increase the yields of existing plant transformation methods by limiting cellular damage and resulting apoptosis (cell death), resulting in higher yields of recovery of viable transformed cells after biolistic, *Agrobacterium tumefaciens*, or electroporation methods are used.

In one embodiment, the present invention comprises a method for producing a genetically modified plant with a selected DNA comprising:
(a) selecting the DNA;
(b) complexing the selected DNA with a water-soluble cationic-fullerene;
(c) incubating plant cells or protoplasts with the DNA/fullerene complex for sufficient time for the DNA to be transported into the plant cell; and
(d) growing the cells or protoplasts into a plant.

In yet another embodiment, the present invention comprises a method for reducing the damage to a selected plant cell or protoplast during the insertion of selected DNA in the selected plant cell or protoplast using plant transformation technology process selected from the group comprising biolistics, electroporation, *Agrobacterium* use, micro injection; and permeability treatments comprising: pre-treating the selected plant cell or protoplast and selected DNA with a sufficient amount of water-soluble fullerene free radical scavenger to reduce the damage caused by the transformation technology.

DETAILED DESCRIPTION OF THE INVENTION

Figure 1:
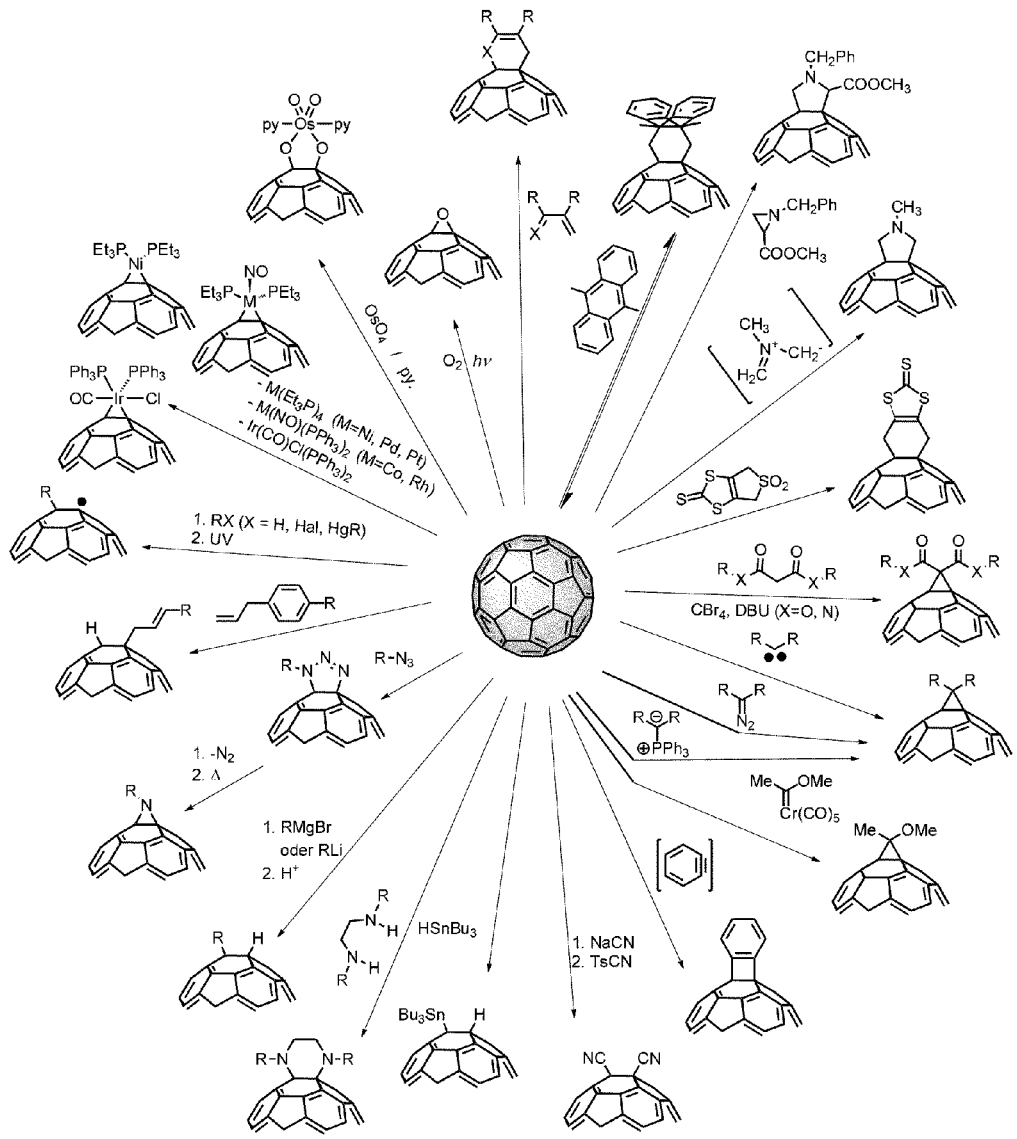
FIG. 1 shows several C-60 functionalizations.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

Definitions

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

The terms "plant genetic transformation" or "plant transformation" refer to methodology that inserts a selected DNA into a plant cell and thereby alters its genetic makeup or genotype. This technique plays a central role in applied plant molecular biology and is used specifically to create genetically modified plants with improved or altered characteristics. Applications of plant transformation techniques have produced significant achievements, including improvements in food crops and also production of valuable plant secondary metabolites. Other plant transformation processes include biolistics, electroporation, *Agrobacterium* use, micro injection, and permeability treatments.

Methods and descriptions of cationic-fullerene compounds, and in one embodiment the cationic-fullerene is an amino-fullerene compounds that are water-soluble are well known in the art. The water-soluble cationic fullerenes are used for the method of producing the genetically modified plant of the present invention. The core fullerene sphere can be "decorated" with multiple side groups to manipulate its transport and binding properties (FIG. 1). Although, the parent fullerene molecule is not water-soluble, when substituted with at least three polar groups, either cationic, anionic, or polar neutral, in one embodiment amino groups, in one embodiment, at least 4 to 6 amino or cationic groups, the compound becomes quite water-soluble. The method of making water soluble fullerenes is well known. All water-soluble fullerenes that are cytoprotective can be used to reduce the damage caused by transformation technology.

Fullerene derivative of the invention in one embodiment are represented generally as Formula I, shown in and represented by $FA_x$
  a) wherein F is an amino-fullerene of C40 to C100 comprising from 1 to 10 cationic or amino groups;
  b) wherein A is an organic cationic functional group that imparts water solubility to the fullerene; and
  c) wherein x is integer from 3 to 10.

In one embodiment the formula above is utilized wherein the Fullerene is further substituted by at least one additional substitution of the formula $B_y$, wherein y is n integer from 1 to 10 and B is a substituent that does not interfere with the water solubility of the fullerene. And each substitution is the same or different.

Figure 2:
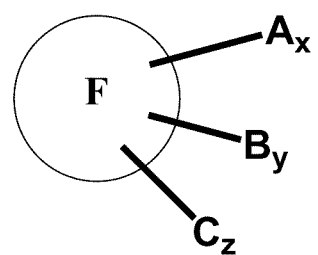
FIG. 2 is the formula for specific embodiment water-soluble fullerenes.

In yet another embodiment the formula shown in FIG. 2 wherein the Fullerene is further substitute by at least one substitution each of $B_y$ and $C_z$ wherein y and z are each an integer of 1 to 10 and each of B and C are the same or different.

These types of fullerenes are known and in one embodiment the fullerenes described in U.S. Pat. Nos. 5,648,523 and 7,163,956 both of which are incorporated by reference in their entirety.

In another embodiment the fullerene is C60 or C70. In yet another embodiment there are 4 to 6 amino groups.

As used herein an "organic cationic functional group" refers to a group that renders the fullerene water-soluble by reason of the cationic or positively-charged groups attached to the surface of the fullerene sphere. In one embodiment it is 3 to 10 cationic groups and in another embodiment it is at least 4 to 6 cationic groups.

As used herein an "organic amino functional group" refers to any amino group that renders the fullerene water-soluble by reason of the amino groups attached to the surface of the fullerene sphere. In one embodiment it is 1 to 10 amino groups in another embodiment at least 4 to 6 amino groups.

As used herein "selected DNA" refers to genomic DNA from any source coding for a trait the user wishes to impart to the plant, it also refers to the use of anti-sense DNA to block or suppress transcription of a gene, the use of SiRNA known as small interfering RNA. Even further, DNA can refer to DNA of the mitochondrial genome (non-chromosomal DNA in the mitochondria) which can also be a target of DNA insertion by the present invention.

As used herein the phrase "complexing the selected DNA with a water-soluble amino-fullerene" refers to the interaction of the Fullerene of the invention (which can be in a cationic form) with the selected DNA to form a non-covalent complex. This complex is capable of entering the plant cell or protoplast and then disassociating to deliver the selected DNA to the cytoplasm, the chromosomal DNA, mitochondrial DNA, or the like. One reference which teaches this association and preparation is Assembly of DNA/Fullerene Hybrid Materials Angew Chem Int Ed. 1998, 37 No 11.

As used herein the term "incubating" refers to mixing a solution or suspension of the fullerene and DNA in water or buffer for a sufficient period of time (known in the art) for the reaction complexation, binding, transport or other chemical or physical event to take place.

As used herein "plant cells or protoplasts" refer to individual units of the selected living plant, either in an intact whole plant or in an isolated state growing on media or agar or in suspension in a growth media or buffer. A "protoplast" refers to a plant cell that has had its protective cell wall partly or totally removed, for example, by enzymatic treatment resulting in an intact biochemical competent unit of living plant that can regenerate the cell wall and further grow into a whole plant under proper growing conditions. As used herein "sufficient time" refers to the time required to complete a given reaction, complexation, binding transport or other chemical or physical event an can range in an embodiment of from just a minute or 2, for 15 minutes to 30 minutes, to several hours, overnight, or the like.

The selected DNA can be contained for delivery to the plant cell or protoplast by being or being part of a plasmid, anti-sense DNA or SiRNA.

As used herein "pretreat" refers to mixing at least one of the cells and selected DNA with the composition of the present invention for a sufficient time for the particular event to take place by itself.

As used herein the term "sufficient amount" of a water-soluble fullerene free radical scavenger refers to an amount sufficient to produce the protective effect of the scavenger during the DNA transformation process utilizing the novel process herein or utilizing the known methods herein.

Figure 4:
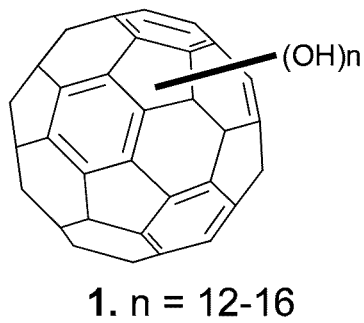
FIG. 4 shows more water-soluble fullerene derivatives.
Figure 4:
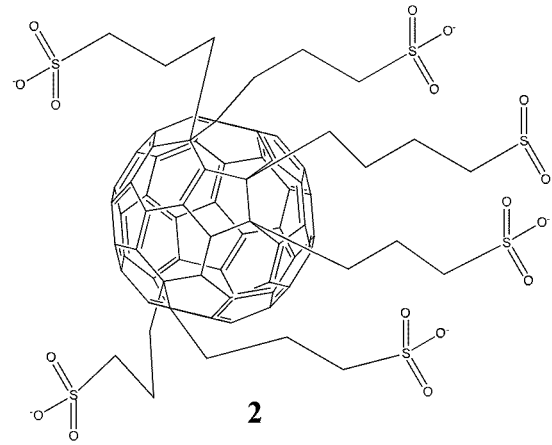
Figure 4:
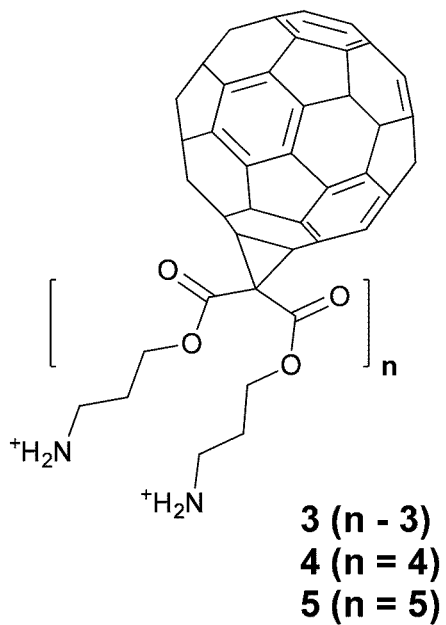
Figure 4:
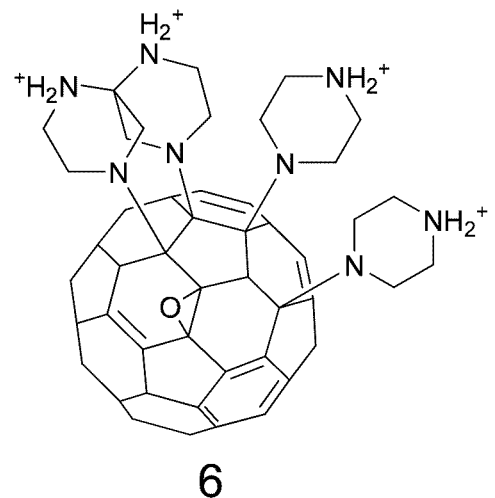

Methods of the invention include the use of water-soluble fullerene derivatives to enhance the yields and improve the performance of standard methods such as biolistics, *Agrobacterium*, micro injection, permeability enhancing gases and electroporation. The invention involves treatment of nucleic acid (DNA, RNA, SiRNA, etc.) with a water-soluble fullerene derivatives or containing from 1% to a large excess with respect to the nucleic acid. In one embodiment the water-soluble fullerene derivative contains 1 to 10 amino groups, in another embodiment, 4 amino groups as shown in FIG. 4.

The nanoparticle interacts with the nucleic acid organizing, compacting, and packaging it into appropriate-sized clusters for endocytosis (transport into cells). Plant cells are then treated with the nanoparticle/nucleic acid complex, either directly or in combination with one of the conventional methods listed above.

Figure 3:
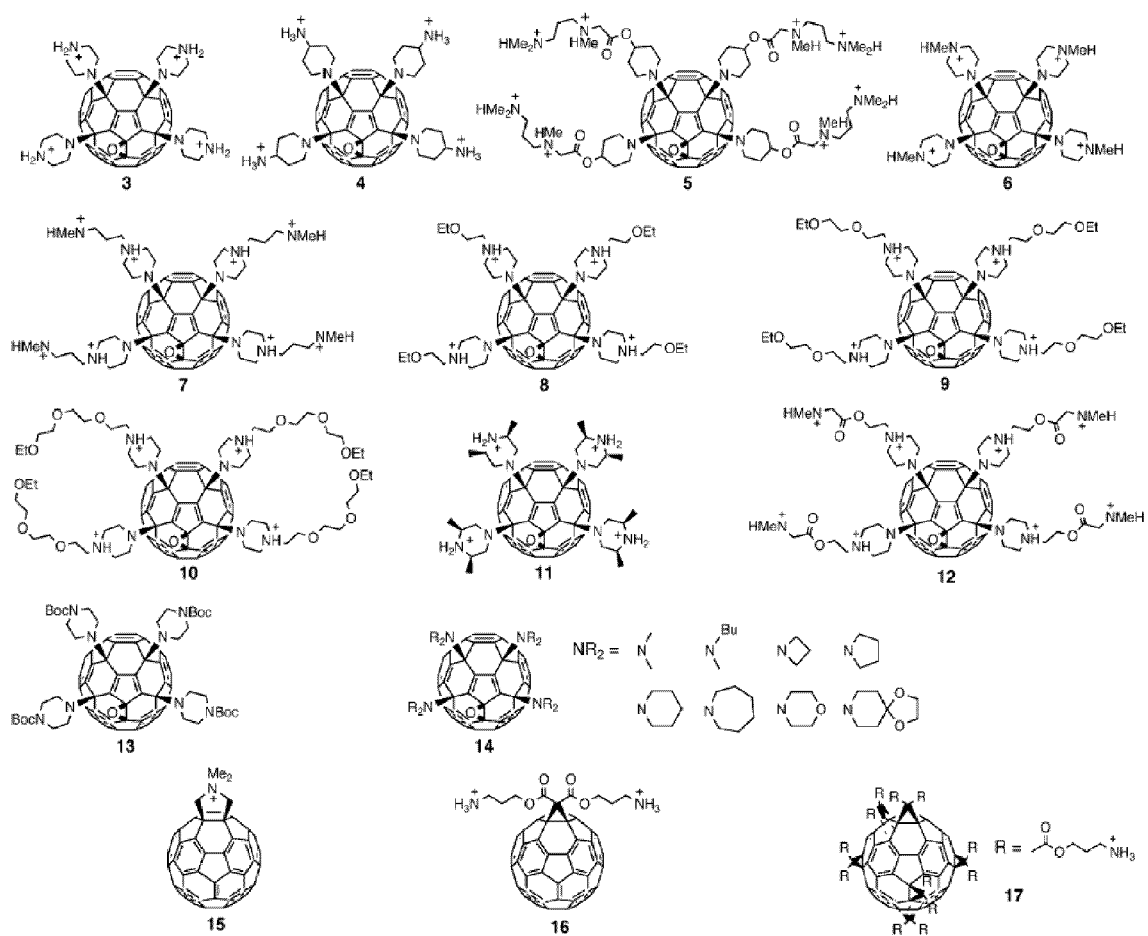
FIG. 3 shows examples of several amino substituted water-soluble Fullerene Derivatives.

We have used a method consisting of synthesized water-soluble fullerene derivative using chemistry, for example, as shown in FIG. 1 by procedures known to those skilled in the art. Embodiments are shown in Formula I (FIG. 2) and have multiple groups attached to the fullerene core. For direct DNA binding and plant transformation, more embodiments involve poly-amino substitutions as illustrated in FIG. 3 and illustrated by the use of compounds 3-6 (FIG. 4). Another embodiment is the use of compound 6 (FIG. 4).

The next step in the method comprises formulation of the water-soluble fullerene derivative in a plant buffer, such as MS buffer (MS media). Plant science uses MS buffer because it somewhat mimics soil-buffer pH. The Moore-Sikora (MS) buffer is illustrative but not a limiting example of a formulation. For every liter of solution, the following quantities of chemicals are dissolved: MES (2-(N-morpholino) ethane-sulfonic acid hydrate ($C_6H_{13}NO_4S.xH_2O$, fw with x of 1=213.25)): 7.43 g; MOPS (3-(N-Morpholino) propane-sulfonic acid ($C_7H_{15}NO_4S$, fw=209.26)): 27.4 g; Boric Acid ($H_3BO_3$, fw=61.83): 13.1 g; Potassium Chloride (KCl, fw=74.56): 74.0 g; Potassium Hydroxide (KOH, fw=56.11): 11.2 g. Add 400 mL deionized water to a 1 L volumetric flask and then quantitatively add each component above to the flask. Use deionized water to rinse out the weighing containers into the flask. Add deionized water to 80% of the final intended volume and stir the solution overnight. Dilute the solution with deionized water to the intended final volume and mix thoroughly. Water-soluble fullerene derivatives of the invention are quite soluble in MS buffer at concentrations up to 1-2 mg/mL (stock solution).

Figure 6:
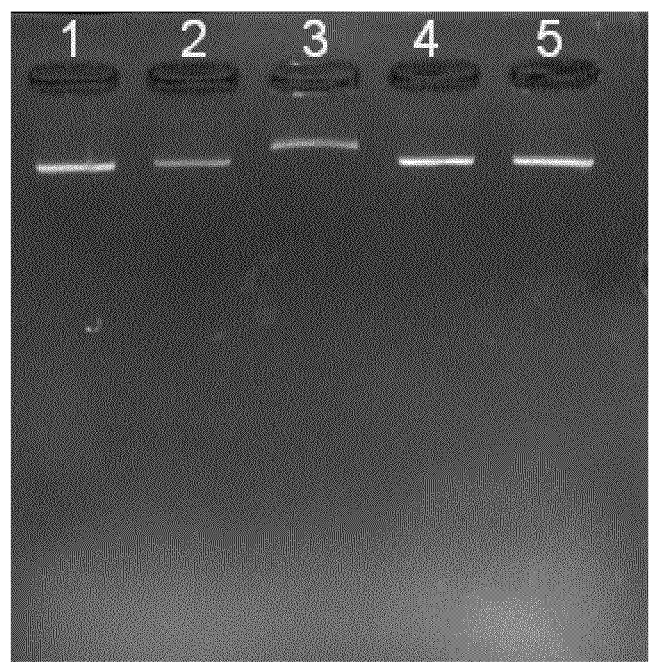
FIG. 6 is a gel Electrophoresis of fullerene derivatives and DNA.

As shown in FIG. 6, 50 ng CAMBIA 1302 plasmid (hereafter plasmid) in TE buffer (a typical recipe for 10:1 TE buffer is 10 mM Tris, bring to pH 8.0 with HCl and add 1 mM EDTA) was added to ~300 ng fullerene derivative diluted in TE buffer from a 0.3 mg/mL stock solution dissolved in distilled water. Each tube was allowed to bind for 15-30 minutes and then place on an agarose gel. FIG. 6 shows Lane 1: plasmid only, Lane 2: Compound 4+plasmid, Lane 3: compound 6+plasmid, Lane 4: compound 1+plasmid, Lane 5 compound 2+plasmid. After running the gel, the bands were visualized using post-staining with commercial SBER SAFE™ 10000× stain. Gel mobility of DNA binding polyamino fullerene compounds 4 and 6 (cationic compounds) were observed as slower moving bands in FIG. 6 Lanes 2 and 3. The non-cationic compounds 1 and 2 showed no DNA binding effect.

Figure 7:
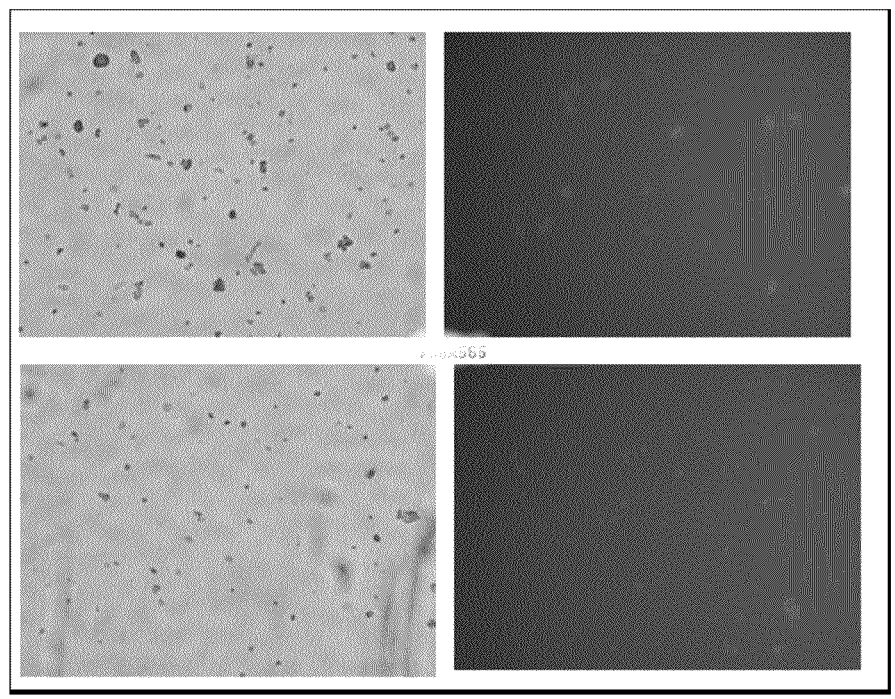
FIGS. 7A and 7B are photo micrograph of Fullerene-enhanced electroporation.
Figure 7:
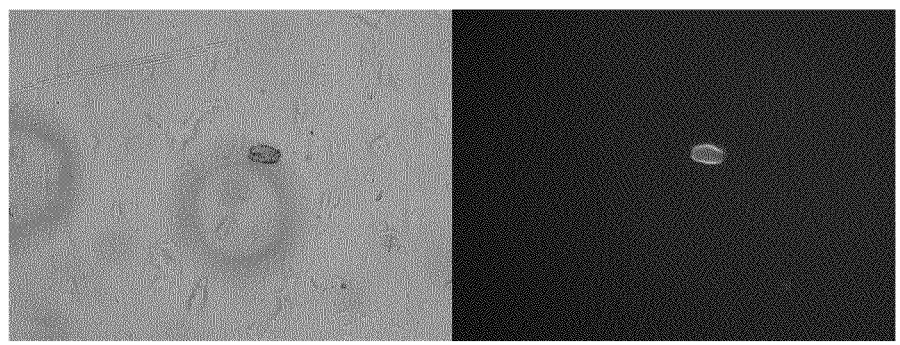

Certain free radical scavenging fullerene nanomaterials enhance the efficiency of common technologies for plant transformation. Using electroporation as an illustrative but not limiting example, we discovered that addition of fullerene nanomaterials improve yields of gene transfer (FIG. 7). Nanoparticle-enhanced nucleic acid delivery methods of the invention improves each of these techniques by increasing the efficiency of the processes, possibly by inhibiting apoptosis and effecting ROS signaling pathways that lead to death of the newly transformed cells. Fullerene compounds are super antioxidants and their free-radical scavenging properties have surprisingly shown a beneficial impact on plant transformation. While the scavenging fullerenes are known, it is not obvious these compositions which have been around for 10 to 20 years and never used for this type of protection would work to any degree and their superior result in this method could not have been predicted from their scavenging activity alone.

Another method of the invention involves use of non-DNA binding compounds such as 1 and 2 to enhance the efficiency and yields of plant transformation methods such as biolistics, *Agrobacterium tumefaciens* methods, and electroporation.

In one method of the invention, DNA in TE buffer (tris/EDTA) was used in combination with one of the common plant transformation methods. One embodiment involves pre-treating the target sample with a water-soluble fullerene derivative of Formula I wherein the groups A, B, and C are groups that enhance free radical scavenging, in another embodiment compounds 1 and 2. The second step uses biolistics, *Agrobacterium tumefaciens* methods, or electroporation method in the standard way. Because of the free radical scavenging effects of the fullerene compound, the yields of DNA insertion and overall plant survival are improved, often by 10% to greater than 50%.

One embodiment of the invention is called fullerene-enhanced electroporation. The method comprises (1) mixing fullerene derivative solution with the DNA of interest, (2) addition of fullerene derivative/DNA solution to plant cells or plant protoplasts, and (3) treatment of the mixture in a Gene Pulser cuvette or similar electroporation apparatus for a few minutes. Suspension was then incubated for 2-3 hours or overnight to allow DNA transfer and gene expression to take place. To demonstrate gene incorporation visually, we employed tobacco cell culture and the DNA encoding green fluorescent protein (GFP) method that is well understood by those skilled in the art. After the GFP gene is expressed, the transformed cells can be seen in the fluorescent microscope by a characteristic green emission that shows that electroporation with fullerene derivative works better than without. FIG. 7A (top) shows wherein electroporation was carried out without addition of a fullerene compound. On the left is the light microscope picture showing tobacco protoplast cells after electroporation. On the right is the fluorescence microscope image showing no GFP expression with only faint auto-fluorescence. FIG. 7 B (bottom) shows electroporation with treatment with water-soluble fullerene derivative polyhydroxy-C60 (compound 1). Left shows the light microscope picture showing tobacco protoplast cells after fullerene-enhanced electroporation. On the right the fluorescence microscope picture shows gene insertion and GFP expression.

An imported method of the invention is not only production of genetically modified, but production of new commercially useful plant-derived materials and products. Beyond the well known agricultural applications, the methods of the invention can be used for producing new plant applications in the fields of energy (cellulosic ethanol, biodiesel, and biobatteries), homeland security (biothreat remediation, phytosensors), clean water (toxin removal), and co-product production (chemical feedstocks or pharmaceuticals).

EXAMPLES

To illustrate the range of fullerene compounds that are subjects of the invention and can be used to enhance plant transformation and whole plant growth, we have prepared a wide range of derivatives to illustrate the diverse functionality that can be used. Neutral or anionic fullerene compounds 1 and 2 and cationic compounds 3-5 and 6 are shown in FIG. 4 and are prepared using chemical methods described below. Neutral or anionic fullerene compounds are designed to be free radical scavengers, whereas cationic fullerene compounds are designed for DNA binding.

Example 1

Preparation of Polyhydroxyl Fullerene 1

A toluene solution containing C60 was stirred for 12 hours with 5 drops of tetrabutylammonium hydroxide (TBAOH, 40% in H2O, Aldrich) and 5 ml of a concentrated aqueous KOH. Following this step, the solvents were removed in vacuo at 50° C. After solvent removal, the reaction mixture was stirred with 20 ml of water/methanol (95/5) for 8 hours, during which time most of the solid dissolved. The supernatant was then vacuum-filtered to obtain a golden-brown aqueous solution. For purification, the solution could be separated on Sephadex G 25 using distilled water. The product C60 (OH)n was collected as a single, pH 6-7 colored band.

Example 2

Preparation of Compound 2

The compound known as FC4S can be prepared from C60 in ~85% yield by treatment of C60 in dimethoxyethane (DME) with sodium naphthilide (10 eq) followed by addition of excess 1,4-butane sultone. The crude product was purified by precipitation from water with methanol.

Example 3

Preparation of Compounds 3-5

A malonate reagent was prepared by treatment of 5 g (2 equiv) of tert-butyl N-(3-hydroxypropyl) carbamate in 250 mL of dry methylene chloride with 1.97 g (1 equiv) of distilled malonyl chloride and 2.21 g (2 equiv) of pyridine. Following purification by column chromatography on silica gel using 1:1 hexane/ethyl acetate as the eluent, 3.20 g (54.7%) of monoamine was obtained. Multiple adducts are prepared in a similar manner, following the progression of the reaction by TLC. Thus, 10 equiv of CBr4, 10 equiv of the tert-butyl N-(3-hydroxypropyl) carbamate-malonate reagent prepared above, and 20 equiv of DBU/CBr4 were subjected to the same reaction conditions as above. Following workup, the crude reaction mixture was separated by silica chromatography.

Example 4

Preparation of Compound 6

The reaction of C60 with Boc-piperazine (6 eq, Aldrich) in chlorobenzene containing cumene hydroperoxide gave the desired Boc-protected product in ~70% yield by precipitation with methanol. Hydrolysis with TFA gives compound 6 which was made up in a 0.3 mg/mL stock solution.

Example 5

Free Radical Scavenging Activity

Figure 5:
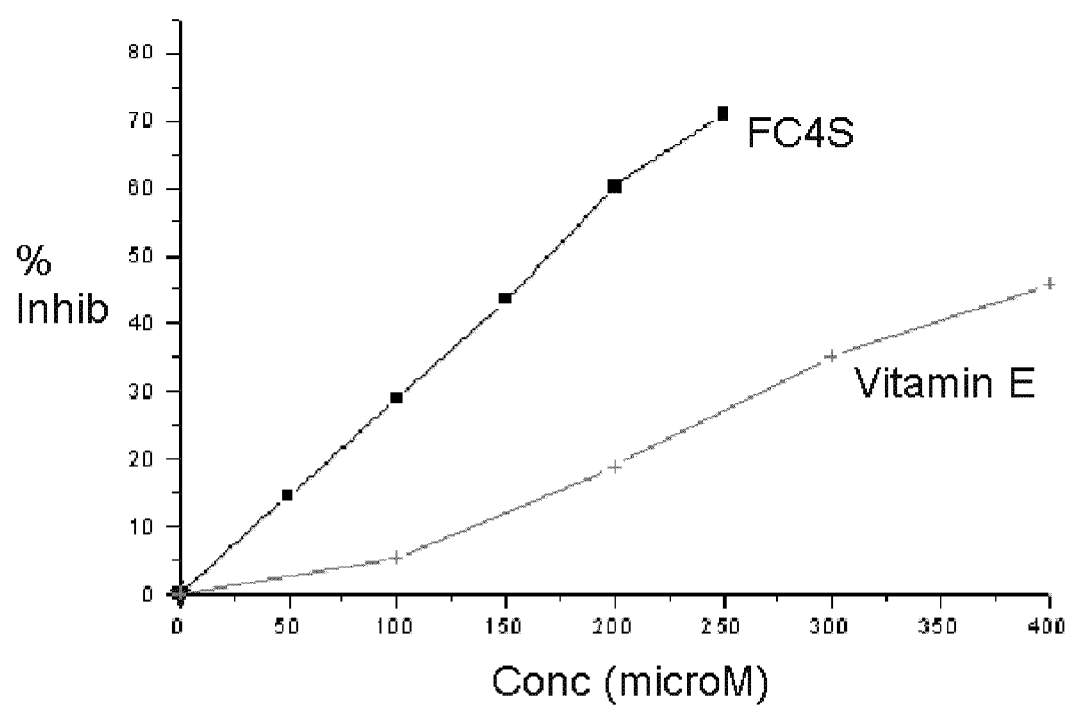
FIG. 5 is a graph of percent inhibition versus concentration for the superoxide scavenging effect for compound 2 vs. Vitamin E.

Tested were superoxide scavenging and radical trapping activities of test compounds 1 and 2 using xanthine/xanthine oxidase/cytochrome C system. The superoxide assay reaction is initiated by the addition of xanthine oxidase ($7.5 \times 10^{-3}$ units) to the incubation mixture and the reaction followed by observing reduction of cytochrome C and the corresponding increase in the absorbance at 550 nm. All assays can be performed at room temperature. The incubation mixture consisted of 50 mM potassium phosphate, 0.1 mM EDTA, 0.01 mM cytochrome C, and 0.05 mM xanthine along with the indicated concentration of antioxidant in a total volume of 3 mL. An example of data obtained from this method with comparing vitamin E and compound 2 is shown in FIG. 5.

Example 6

Figure 8:
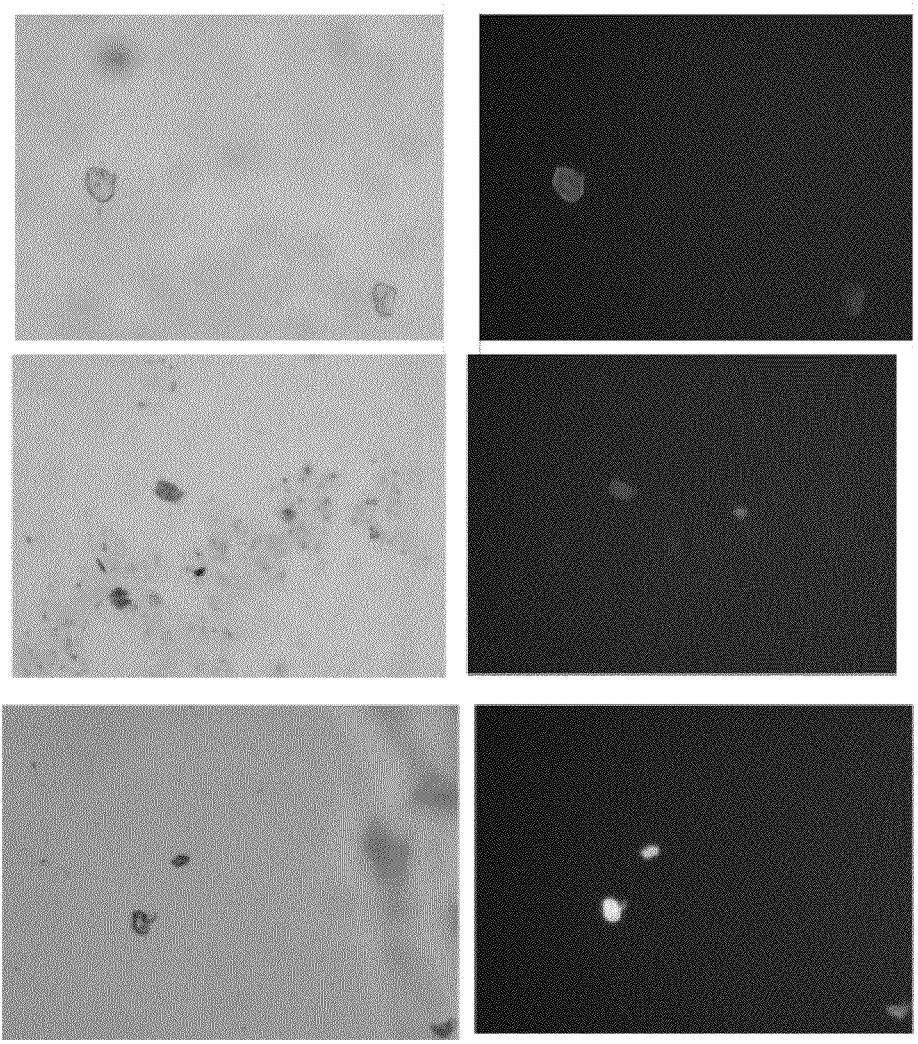
FIG. 8 is a photo micrograph of DNA Binding titration with plasmid DNA.

DNA binding was measured at different fullerene nanoparticle/DNA ratios. The DNA-binding ability of the fullerene test compounds 1, 2, 4, and 6 was examined by direct DNA binding and agarose gel electrophoresis. Neutral free radical scavenger compounds 1 and 2 show no binding to DNA, whereas cationic compounds 4 and 6 show different degrees of DNA binding with observed changes in gel mobility (FIG. 6). In each case, 50 ng plasmid DNA was preincubated for 30 minutes with 100-300 nG fullerene compound (FIG. 8). The DNA binding titration of plasmid pCAMBIA 1302 with compound 6 was carried with 50 nG pCAMBIA 1302 and various concentrations (93-3000 nG per 10 microL). Results shown in FIG. 8 indicate optimal binding at a concentration of ~5-6 equivalents fullerene per DNA. FIG. 8 Lane 1: 50 ng of DNA Plasmid DNA only, Lane 2: 50 ng of DNA Plasmid DNA+ 3000 ng compound 6 (50 equiv), Lane 3: 50 ng of DNA Plasmid DNA+1500 ng compound 6 (25 equiv), Lane 4: 50 ng of DNA Plasmid DNA+750 ng compound 6 (12 equiv), Lane 5: 50 ng of DNA Plasmid DNA+375 ng compound 6 (6 equiv), Lane 6: 50 ng of DNA Plasmid DNA+187 ng compound 6 (3 equiv), Lane 7: 50 ng of DNA Plasmid DNA+93 ng compound 6 (1.5 equiv). Compound 6 stock solution (0.3 mg/mL) was diluted with TE buffer and 10 microL each fullerene dilution was reincubated with plasmid for 30 prior to loading on the gel.

Example 7

Experiments to test the fullerene nanoparticles for transformation ability used tobacco protoplasts for transient assays. Sterile suspension cultures (5% w/v) of tobacco (*Nicotiana tabacum*) were grown in MS basal salts media. Suspension cells were incubated in enzyme solution (0.6 M mannitol, 10 mM MES, 1% Cellulase, 0.2% pectinase) at pH 5.7 in the dark, at 24° C. overnight. After incubation, protoplasts were passed through 100 μM nylon mesh, washed and protoplasts pelleted by centrifugation. Protoplasts were resuspended in the appropriate media required for transformation studies.

Figure 9:
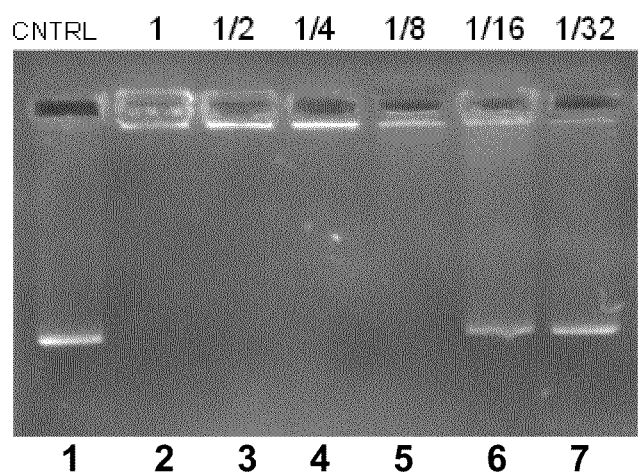
FIG. 9 is a gel electrophoresis of a plant transformation with a water-soluble Fullerene Derivative.

Our initial experiments have used the GFP construct pCAMBIA 1302 plasmid (www.cambia.org)+fullerene nanoparticle combination (in 1× medium). The DNA/fullerene nanoparticle complex was preformed (using several concentrations near the optimal binding as shown above) prior to incubation with typically $5 \times 10^5$ protoplasts at various amounts per reaction mix (3 ml). Controls utilize naked DNA (no fullerene). Following overnight incubation as above, cells expressing GFP were evaluated through fluorescence microscopy. FIG. 9 (left) shows field microscopy images of tobacco protoplast cells treated with pCAMBIA 1302 plasmid DNA bound to water-soluble fullerene compound 6. On the right is the fluorescence microscope image of the same area showing GFP expression. The percentage of transformed cells relative to the total number of cells was determined and a control of DNA alone (no fullerene compound) was carried out showing no transformation.

Example 8

Method for Use of Water-soluble Fullerene Derivative for Yield Enhancement of the Electroporation Technique Electroporation is the process where cells are mixed with a DNA construct and then briefly exposed to pulses of high voltage. The cell membrane of the host cell is temporarily made penetrable thereby allowing foreign DNA to enter the host cell. Some of these cells will incorporate the new DNA and express the desired gene. While direct introduction of DNA by electroporation has proven successful, in some cases, the electroporation technique is not as commonly used in comparison to other transformation methods. Isolated protoplasts ($5 \times 10^5$) were pelleted and resuspended in electroporation buffer. To this, differing amounts of either CAMBIA 1302 plasmid DNA alone or DNA and polyhydroxy-C60 in the same buffer, were added. Electroporation was carried out using a Bio-Rad Gene Pulser electroporation system. Following electroporation, protoplasts were cultured overnight in the dark in 1× medium, and then assessed for percentage of protoplasts exhibiting GFP expression. These experiments indicate if the use of a fullerene nanoparticle carrier confers any advantage over free DNA alone in terms of transformation ability (FIG. 7).

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

The invention claimed is:

1. A method for producing a genetically modified plant with a selected DNA comprising:
   (a) selecting the DNA;
   (b) complexing the selected DNA with a spherical water-soluble cationic-amino-fullerene;
   (c) incubating plant cells or protoplasts with the DNA/fullerene complex for sufficient time for the DNA to be transported into the plant cell;
   (d) regenerating the cells or protoplasts into a plant; and
   (e) wherein said water-soluble fullerene comprises a fullerene derivative of formula $FA_x$,
      i. wherein F is a fullerene of C60;
      ii. wherein A is an organic cationic amino functional group which imparts water solubility to the fullerene; and
      iii. wherein x is an integer from 3 to 10.

2. The method of claim 1, wherein the DNA of interest is incorporated into a plasmid; or wherein the DNA of interest is anti-sense DNA, or encodes siRNA, or a part thereof.

3. The method according to claim 1 wherein the fullerene comprises from 4 to 6 cationic groups.

4. The method according to claim 1 wherein the fullerene is further substituted by at least one additional substitution of the formula $B_y$, wherein y is an integer from 1 to 10 and B is a substituent that does not interfere with the water solubility of the fullerene wherein each substitution is the same or different.

5. The method according to claim 1 wherein the fullerene is further substituted by at least one substitution each of $B_y$ and $C_z$ wherein y and z are each an integer of 1 to 10 and each of B and C are the same or different.

6. A method for reducing the damage to a selected plant cell or protoplast due to free radical damage during the insertion of selected DNA into the selected plant cell or protoplast using a plant transformation technology process selected from the group consisting of biolistics, electroporation, *Agrobacterium* use, micro injection and permeability treatments, comprising:
   pre-treating the selected plant cell or protoplast and selected DNA prior to transformation with a sufficient amount of spherical water-soluble neutral or anionic amino fullerene free radical scavenger to reduce the damage caused by free radicals during the transformation technology, wherein said water-soluble fullerene is a fullerene derivative of formula $FA_x$,
   a) wherein F is a fullerene of C60;
   b) wherein A is an organic amino functional group which imparts water solubility to the fullerene; and
   c) wherein x is an integer from 3 to 10.

7. The method of claim 6, wherein said plant transformation technology employs *Agrobacterium*.

8. The method of claim 6, wherein said plant transformation technology employs biolistics.

9. The method of claim 6, wherein said plant transformation technology employs electroporation.

10. The method according to claim 6 wherein the fullerene comprises from 4 to 6 amino groups.

11. The method according to claim 6 wherein the fullerene is further substituted by at least one additional substitution of the formula $B_y$, wherein y is an integer from 1 to 10 and B is a substituent that does not interfere with the water solubility of the fullerene, wherein each substitution is the same or different.

12. The method according to claim 6 wherein the fullerene is further substituted by at least one substitution each of $B_y$ and $C_z$, wherein y and z are each an integer of 1 to 10 and each of B and C are the same or different.

* * * * *